United States Patent [19]

Kondo et al.

[11] 4,169,199
[45] Sep. 25, 1979

[54] PRECURSORS FOR PROSTAGLANDIN ANALOGUE AND PROCESS FOR PREPARING THE SAME

[75] Inventors: Kiyosi Kondo, Yamato; Daiei Tunemoto, Sagamihara; Yuriko Takahatake, Tokyo, all of Japan

[73] Assignee: Sagami Chemical Research Center, Tokyo, Japan

[21] Appl. No.: 862,328

[22] Filed: Dec. 20, 1977

[30] Foreign Application Priority Data

Dec. 27, 1976 [JP] Japan ................................. 51-156361
Dec. 27, 1976 [JP] Japan ................................. 51-156362
Dec. 27, 1976 [JP] Japan ................................. 51-156363

[51] Int. Cl.$^2$ ............................................. C07D 309/10
[52] U.S. Cl. ................................. 542/413; 204/158 R; 260/343.3 R; 260/343.6
[58] Field of Search .................... 204/158 R; 542/413; 260/343.3

[56] References Cited

U.S. PATENT DOCUMENTS

| | | | |
|---|---|---|---|
| 3,787,448 | 1/1974 | Himizu et al. | 260/343.6 |
| 3,850,952 | 11/1974 | Kuo et al. | 260/343.6 |
| 3,859,188 | 1/1975 | Libit | 204/158 R |
| 3,993,664 | 11/1976 | Libit | 204/158 R |
| 4,088,779 | 5/1978 | Vlattas | 542/413 |

OTHER PUBLICATIONS

Himizu et al. Chem. Abstracts 78(1973) #147776.
Hauser et al., Tet. Letters 11(1974) pp. 905–908.
Aries, Chem. Abst. 83(1975) #193064.

Primary Examiner—Arthur P. Demers
Attorney, Agent, or Firm—Sughrue, Rothwell, Mion, Zinn and Macpeak

[57] ABSTRACT

Bicyclolactone compounds represented by the formula (I)

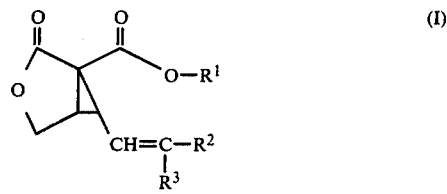

wherein $R^1$ represents an alkyl group having 1 to 4 carbon atoms, $R^2$ represents a substituted or unsubstituted alkyl group having 1 to 8 carbon atoms and $R^3$ represents a hydrogen atom or an alkyl group having 1 to 4 carbon atoms;

γ-lactone sulfide or sulfoxide compounds represented by the formula (II)

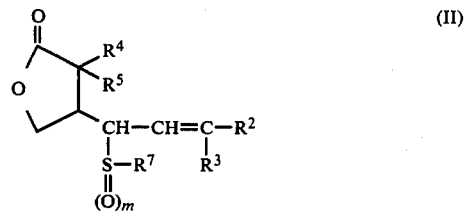

wherein $R^2$ and $R^3$ are as defined above, $R^4$ represents a hydrogen atom or a —COOR$^1$ group wherein $R^1$ is as defined above, $R^5$ represents a hydrogen atom or a —CH$_2$—Y—(CH$_2$)$_n$—COOR$^6$ group wherein Y represents a —CH$_2$CH$_2$— group or a —CH=CH— group, $R^6$ represents a hydrogen atom or an alkyl group having 1 to 4 carbon atoms and n is an integer of 0 to 6, $R^7$ represents an alkyl group having 1 to 4 carbon atoms or an aryl group and m is 0 or 1, useful as precursors for prostaglandin analogues; and process for preparing the same.

1 Claim, No Drawings

PRECURSORS FOR PROSTAGLANDIN ANALOGUE AND PROCESS FOR PREPARING THE SAME

BACKGROUND OF THE INVENTION

1. Field of the Invention

This invention relates to precursors for prostaglandin analogues and processes for preparing the same. More particularly, this invention relates to bicyclolactone compounds and γ-lactone sulfide and sulfoxide compounds represented by the formulae (I) and (II), respectively, hereinafter described which are useful as precursors for the synthesis of prostaglandin analogues, that is, 10-oxaprostaglandins, having biological properties similar to prostaglandin compounds, and processes for prepring such precursors for prostaglandin analogues.

2. Description of the Prior Art

It is well known that the naturally-occurring prostaglandin compounds are composed of 20 carbon atoms and contain in the structure thereof a cyclopentanone ring and exist broadly in the brain, lung, kidney, semen, uterus membrane, etc. of living body. These prostaglandin compounds are also known to have a wide variety of excellent pharmacological activities such as anti-ulcer, hypotensive, anti-asthmatic, uterotonic activities depending upon critical differences in the chemical structure of prostaglandin compounds, and recently the synthesis of prostaglandin compounds has been extensively studied.

Further, it has been found that the prostaglandin compounds having a hetero atom, e.g., an oxygen, nitrogen or sulfur atom, as a ring member of the cyclopentane ring also possess activities similar to those of naturally-occurring prostaglandin, as reported in *Taisha* (Metabolism), Vol. 21, 1461 (1975). In particular, prostanoic acid as a basic structure of prostaglandin compounds in which the carbon atom at the 10-position is replaced by an oxygen atom is called as 10-oxaprostanoic acid and various methods for the synthesis of 10-oxaprostanoic acid have been reported. For example, a lactone ring as a basic structure can be produced by oxidation of a cyclooctene compound, as described in F. M. Hauser and R. C. Hoffman, Tetrahedron Letters, 905 (1974), or by condensation of a succinic acid ester with formaldehyde, as described in Japanese Patent Application Laid Open to Public Inspection Nos. 8773/1973 and 8774/1973.

The above conventional methods for the formation of a lactone ring possess certain characteristic features, but are not advantageous in that these methods require expensive reagents for the carbon-carbon extension reaction and are unable to produce selectively specific stereoisomers required for producing pharmacologically active prostaglandin compounds. Particularly, in the above conventional methods, it is difficult to produce stereospecifically a compound having an α-configuration of hydroxy group at the 15-position which is required for the structure of naturally-occurring prostaglandin.

SUMMARY OF THE INVENTION

An object of the present invention is to provide novel bicyclolactone compounds represented by the formula (I)

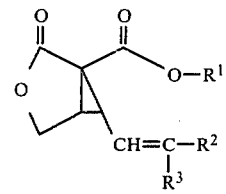

wherein $R^1$ represents an alkyl group having 1 to 4 carbon atoms, $R^2$ represents a substituted or unsubstituted alkyl group having 1 to 8 carbon atoms and $R^3$ represents a hydrogen atom or an alkyl group having 1 to 4 carbon atom; and γ-lactone sulfide and sulfoxide compounds represented by the formula (II)

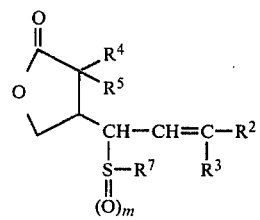

wherein $R^2$ and $R^3$ are as defined above, $R^4$ represents a hydrogen atom or a —COOR$^1$ group wherein $R^1$ is as defined above, $R^5$ represents a hydrogen atom or a —CH$_2$—Y—(CH$_2$)$_n$—COOR$^6$ group wherein Y represents a —CH$_2$CH$_2$— group or a —CH=CH— group, $R^6$ represents a hydrogen atom or an alkyl group having 1 to 4 carbon atoms and n is an integer of 0 to 6, $R^7$ represents an alkyl group having 1 to 4 carbon atoms or an aryl group and m is 0 or 1.

Another object of the present invention is to provide a process for preparing the above bicyclolactone compounds of the formula (I).

A further object of the present invention is to provide a process for preparing the above γ-lactone sulfide and sulfoxide compounds of the formula (II).

DETAILED DESCRIPTION OF THE INVENTION

As a result of extensive studies on the process for preparing prostaglandin analogues, it was found that the precursors and the processes of the present invention provide expedient means for the synthesis of prostaglandin analogues.

The term "alkyl group having 1 to 4 carbon atoms" as used herein for $R^1$, $R^3$, $R^6$ and $R^7$ means a straight or branched chain alkyl group having 1 to 4 carbon atoms and includes, for example, a methyl, ethyl, propyl, isopropyl, n-butyl, sec-butyl or tert-butyl group.

The term "substituted or unsubstituted alkyl group having 1 to 8 carbon atoms" as used herein for $R^2$ means a straight or branched alkyl group having 1 to 8 carbon atoms and includes, in addition to the examples of the alkyl group having 1 to 4 carbon atoms given above, a pentyl, hexyl, heptyl, octyl groups which may be substituted with an —O— alkyl group or a —S-alkyl group wherein the alkyl moiety can be a straight or branched chain and has 1 to 4 carbon atoms, or a phenoxy group which may be substituted with a halogen atom or an alkyl group having 1 to 4 carbon atoms.

The term "aryl group" as used herein for $R^7$ means an unsubstituted or substituted phenyl group wherein the substituent is a halogen atom, an alkyl or alkoxy group having 1 to 4 carbon atoms.

The term "halogen" as used herein includes fluorine, chlorine, bromine and iodine.

The γ-lactone sulfide or sulfoxide compounds represented by the formula (II) include the compounds represented by the formulae (IIa), (IIb), (IIc), (IId) and (IIe) given below.

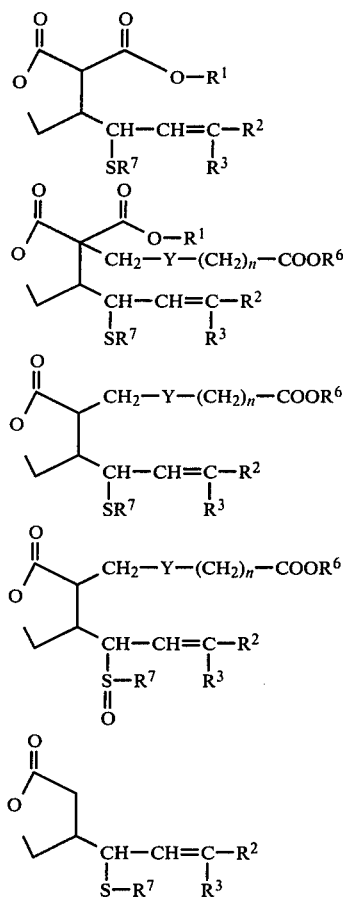

The bicyclolactone compounds of the formula (I) and γ-lactone sulfide or sulfoxide compounds of the formula (II) of the present invention can be prepared according to the processes shown in the Reaction Scheme below:

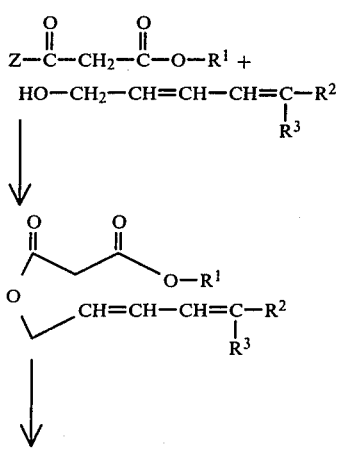

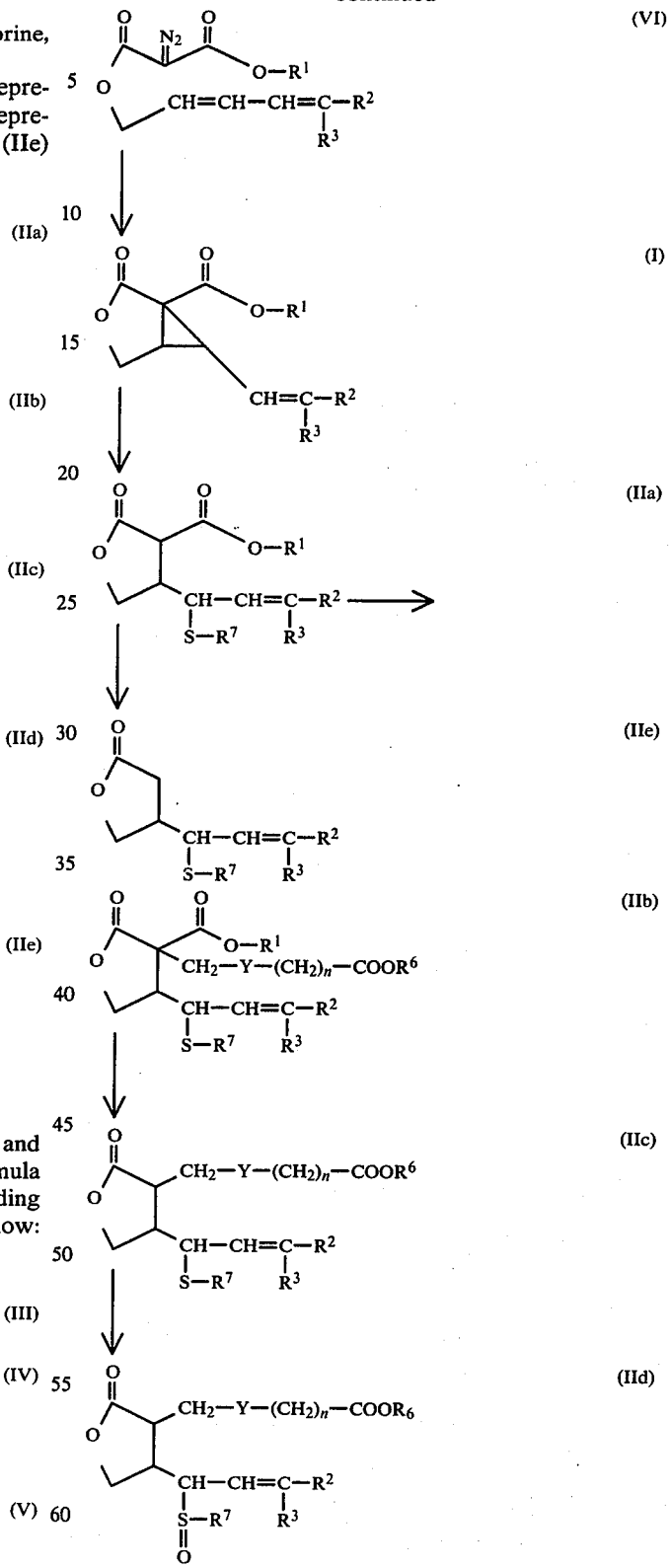

wherein $R^1$, $R^2$, $R^3$, $R^6$, $R^7$, Y and n are as defined above, and Z represents a halogen atom.

According to the present invention, there is provided a process for preparing a compound of the formula (IId)

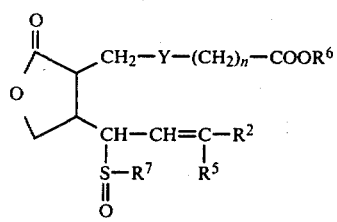
(IId)

wherein $R^2$ represents a substituted or unsubstituted alkyl group having 1 to 8 carbon atoms, $R^3$ and $R^6$ each represents a hydrogen atom or an alkyl group having 1 to 4 carbon atoms, $R^7$ represents an alkyl group having 1 to 4 carbon atoms or an aryl group, Y represents a —$CH_2CH_2$— group or a —CH=CH— group, and n is an integer of 0 to 6, which comprises subjecting a diazomalonic acid ester represented by the formula (VI)

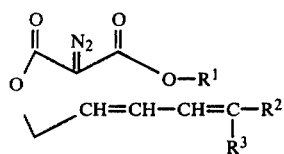
(VI)

wherein $R^2$ and $R^3$ are as defined above and $R^1$ represents an alkyl group having 1 to 4 carbon atoms, to a carbene or carbenoid formation either by a catalytic reaction or a photo-decomposition to produce a bicyclolactone compound of the formula (I)

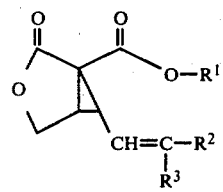
(I)

wherein $R^1$, $R^2$ and $R^3$ are as defined above, reacting the thus obtained bicyclolactone compound with a mercaptan compound of the formula (VII)

$R^7$-SH               (VII)

wherein $R^7$ is as defined above, in the presence of a base to produce a γ-lactone sulfide compound of the formula (IIa)

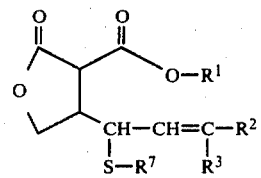
(IIa)

wherein $R^1$, $R^2$ and $R^7$ are as defined above, reacting the thus obtained γ-lactone sulfide compound with an alkylating agent of the formula (VIII)

Z—$CH_2$—Y—$(CH_2)_n$—$COOR^6$     (VIII)

wherein $R^6$, Y and n are as defined above, and Z represents a halogen atom, a tosyloxy group or an acyloxy group, in the presence of a base to produce a compound of the formula (IIb)

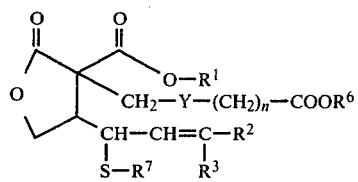
(IIb)

wherein $R^1$, $R^2$, $R^3$, $R^6$, $R^7$, Y and n are as defined above, subjecting the thus obtained compound of the formula (IIb) to either (1) heat-treatment at a temperature of about 50° to about 200° C. in the presence of an alkali metal compound and inert polar solvent, or (2) an acid or alkali hydrolysis at a temperature of about 0° C. to about 150° C. followed by heat treatment at a temperature of about 50° to about 200° C. to produce a compound of the formula (IIc)

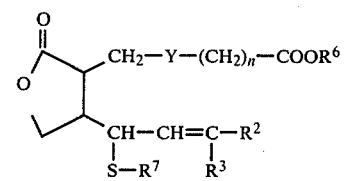
(IIc)

wherein $R^2$, $R^3$, $R^6$, $R^7$, Y and n are as defined above, and oxidizing the thus obtained compound of the formula (IIc) with an oxidizing agent in an inert solvent.

Also, the present invention provides a process for preparing a compound of the formula (IIe)

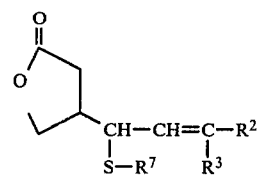
(IIe)

wherein $R^2$, $R^3$ and $R^7$ are as defined above, which comprises subjecting a γ-lactone sulfide compound of the formula (IIa) to either (1) heat-treatment at a temperature of about 50° to about 200° C. in the presence of an alkali metal compound and an inert polar solvent, or (2) an acid or alkali hydrolysis at a temperature of about 0° C. to about 150° C. followed by heat-treatment at a temperature of about 50° to about 200° C.

The bicyclolactone compounds of the present invention represented by the formula (1) have an ester group at the 1-position and a carbonyl group at 2-position and thus the cyclopropane ring of the compounds can easily be opened when the compound is reacted with a nucleophilic reagent to selectively produce the corresponding γ-lactone compound having the formula (II).

Generally, in the ring-opening and addition reaction between a vinyl-substituted cyclopropane compound and a nucleophilic reagent, the unsaturated double bond of the vinyl moiety occasionally takes part in the reaction thereby giving rise to a so-called conjugated addition product as described in J. M. Stewart et al., J. Org. Chem. 34, 7 (1969). However, in accordance with the process of this invention, it was found that the alkenyl group attached to the 6-position of the bicyclo compound of the formula (I) does not affect the above ring-opening and addition reaction thereby producing a γ-lactone compound of the formula (IIa).

The γ-lactone compounds of the formula (IIa) are very useful as precursors for producing prostaglandin analogues, i.e., oxaprostaglandins, since the compounds of the formula (IIa) possess all the functional groups required for converting into oxaprostaglandin compounds, i.e., an ester group at 2-position and an allylic sulfide group at 3-position of the lactone ring.

More specifically, it is possible to selectively introduce an additional substituent at the 2-position of the lactone ring since the ester group as an activating group is present at the 2-position, as illustrated hereinafter in detail for the production of compounds of formula (IIb).

Further, the ester activating group present at the 2-position can be removed easily and selectively after introduction of the additional substituent into the 2-position, as illustrated hereinafter in detail for the production of compounds of the formulae (IIc) and (IIe).

Still further, the allylic sulfide group in the chain attached to the 3-position of the γ-lactone compounds of the formula (IIa) can easily be converted into an allylic alcohol group which is essencial for the ω-chain of prostaglandin analogues, via oxidation and rearrangement reactions, as illustrated hereinafter in detail for conversion of the compound of the formula (IIc)-→(IId)→10-oxaprostanoic acid derivatives.

Thus, the above characteristic features of the compounds of this invention and the processes of this invention can provide ideal synthetic procedures for producing side chains attached to the lactone ring of the oxaprostaglandin compounds.

The processes according to the present invention are further illustrated below in greater detail.

The starting materials of the formula (VI) can be prepared by reacting a malonic acid half ester halide of the formula (III)

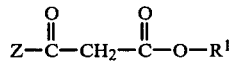 (III)

wherein $R^1$ and Z are as defined above, with a dienyl alcohol of the formula (IV)

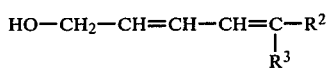 (IV)

wherein $R^2$ and $R^3$ are as defined above, under basic conditions to produce an alkylalkadienyl malonate of the formula (V)

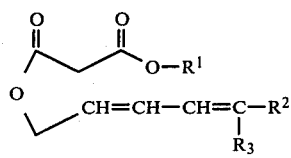 (V)

wherein $R^1$, $R^2$ and $R^3$ are as defined above, and diazotizing the resulting compound of the formula (V) with a diazotizing agent.

The malonic acid half ester halide of the formula (III) are commercially available or can easily be prepared from malonic acid. Also, the dienyl alcohol of the formula (IV) can be easily prepared from the corresponding dienyl aldehyde or a dienylcarboxylic acid ester by reduction.

The reaction between the malonic acid half ester halide of the formula (III) and a dienyl alcohol (IV) can be carried out under basic conditions, for example, in the presence of an organic amine such as triethylamine, tributylamine, dimethylaniline, pyridine, piperidine and the like in an approximately equimolar amount relative to the reactants, at a temperature of about 0° to about 100° C., preferably at room temperature for about 1 to about 24 hours. The reaction can be carried out without solvents, but in order to improve the yield of the desired product (III) under mild reaction conditions, a solvent such as acetonitrile, dimethylformamide, tetrahydrofuran, diethyl ether, methylene chloride and the like can preferably be used.

The resulting alkylalkadienyl malonate of the formula (V) is then diazotized with a diazotizing agent. The diazotization generally proceeds smoothly at room temperature (about 15° to 30° C.) without heating or cooling under atmospheric pressure.

Suitable examples of diazotizing agents which can be used in the above diazotization are azide compounds such as tosyl azide, benzene-sulfonyl azide, phenyl azide, azidoformate and the like which are well known in the art.

Suitable examples of bases which can be used in the above diazotization reaction are alkali metal hydroxides such as sodium hydroxide, potassium hydroxide and the like, alkali metal alkoxides such as sodium methoxide, sodium ethoxide, sodium t-butoxide, potassium t-butoxide and the like, the organic amines such as triethylamine, tributylamine, dimethylaniline, pyridine, piperidine and the like. These bases can preferably be used in an equimolar amount relative to the alkylalkadienyl malonate of the formula (V).

Typical examples of the starting materials of the formula (VI) thus obtained are methyl 2,4-decadienyl diazomalonate, ethyl 2,4-decadienyl diazomalonate, t-butyl 2,4-decadienyl diazomalonate, methyl 2,4-nonadienyl diazomalonate, methyl 2,4-undecadienyl diazomalonate, methyl 5-methyl-2,4-decadienyl diazomalonate, methyl 4-methyl-2,4-decadienyl diazomalonate, methyl 6-phenoxy-2,4-hexadienyl diazomalonate and the like.

The bicyclolactone compounds of the formula (I) can then be prepared by subjecting the diazomalonate compound of the formula (VI) to carbene or carbenoid formation conditions by taking advantage of an intramolecular addition of the compound of the formula (VI).

Generally, in carbene formation by decomposition of such diazo compounds, various reactions may occur and hence the reaction product can be expected to be a mixture of different products, but in accordance with the process of this invention, it is found that the compound of the formula (VI) can be selectively converted into the desired bicyclolactone compound of the formula (I).

The carbene or carbenoid formation can be attained by either (1) a catalytic method or (2) a photodecomposition method.

The catalytic method can be achieved by catalyzing the starting material of the formula (VI) in the presence of a trace amount of a catalyst such as a metal or a metal salt, for example, copper powder, copper bronze, copper halides, copper sulfate, acetylacetonate-copper, copper phosphine complex, silver oxide, silver nitrate and the like, in an inert atmosphere thereby obtaining a corresponding carbenoid.

The photodecomposition method can be achieved by exposing the starting material of the formula (VI) to the light directly or through an inert atmosphere thereby obtaining a corresponding carbene. The light sources which can be used in the photodecomposition can be those usually employed in chemical industries, for example, low-pressure or high-pressure mercury lamps.

In both catalytic and photodecomposition methods, a solvent is not necessarily required, but the above methods can preferably be conducted using a solution of the starting material of the formula (VI) in an inert solvent and in an inert atmosphere in order to minimize the formation of by-products and to improve the reaction selectivity to the desired product. Typically, the above methods can be advantageously carried out in an inert atmosphere such as nitrogen or argon gas and in an inert solvent such as benzene, toluene, xylene, hexane, petroleum ether and the like.

The carbene or carbenoid formed as described above immediately gives rise to cyclization selectively with the double bond present in the molecule thereof to produce a bicyclolactone compound of the formula (I) in high yield.

Typical examples of the bicyclolactone compounds of the formula (I) thus formed are:
methyl 6-(trans-1-heptenyl)-3-oxa-2-oxo-bicyclo[3.1.0]-hexane-1-carboxylate,
ethyl 6-(trans-1-heptenyl)-3-oxa-2-oxo-bicyclo[3.1.0]-hexane-1-carboxylate,
isopropyl 6-(trans-1-heptenyl)-3-oxa-2-oxo-bicyclo[3.1.0]-hexane-1-carboxylate
methyl 6-(trans-1-hexenyl)-3-oxa-2-oxo-bicyclo[3.1.0]-hexane-1-carboxylate,
methyl 6-(trans-1-octenyl)-3-oxa-2-oxo-bicyclo[3.1.0]-hexane-1-carboxylate,
methyl 6-(3-methyl-trans-1-heptenyl)-3-oxa-2-oxo-bicyclo[3.1.0]hexane-1-carboxylate,
methyl 6-(2-methyl-trans-1-heptenyl)-3-oxa-2-oxo-bicyclo[3.1.0]hexane-1-carboxylate,
methyl 6-[3-(m-trifluoromethyl)phenoxy-1-propenyl]-3-oxa-2-oxo-bicyclo[3.1.0]hexane-1-carboxylate, and the like.

The bicyclolactone compounds of the formula (I) obtained as above can then be converted into the corresponding lactone compounds of the formula (IIa) by ring-opening of the cyclopropyl group present in the molecule through a reaction with a mercaptan compound of the formula (V)

$$R^7\text{-SH} \qquad (V)$$

wherein $R^7$ represents an alkyl group having 1 to 4 carbon atoms or an aryl group; or a mercaptide of the mercaptan compound of the formula (V); in the presence of a base to form a compound of the formula (IIa).

The reaction between a bicyclolactone compound of the formula (I) and a mercaptan compound of the formula (V) can be carried out at a temperature of about 0° to about 100° C., preferably at room temperature using about 1 mol of the mercaptan compound per mol of the compound of the formula (I) in the presence of a base.

Suitable examples of base which can be used in the above reaction are alkali metal hydroxides such as potassium hydroxide, sodium hydroxide and the like, alkali metal alkoxides such as sodium methoxide, potassium methoxide, sodium ethoxide, potassium t-butoxide and the like, and organic amines such as triethylamine, tributylamine, pyridine and the like. A so-called catalytic amount of the base is generally sufficient but the use of an equimolar amount of the base relative to the compound of the formula (I) is preferred for reducing the reaction time required for completing the reaction and also increasing the yield of the desired product of the formula (IIa).

The base used in the above reaction is considered to function as first reacting with a mercaptan compound of the formula (V) in the reaction system to product a mercaptide anion. The mercaptide anion thus formed appears to attack the bicyclo nucleus of the compound of the formula (I) thereby resulting in a partial ring-opening of the bicyclo nucleus to produce a salt comprising an anion of the compound of the formula (IIa) and the anion is then converted into a compound of the formula (IIa), as illustrated below where an alkali metal hydroxide (MOH, M is an alkali metal) is used as a base.

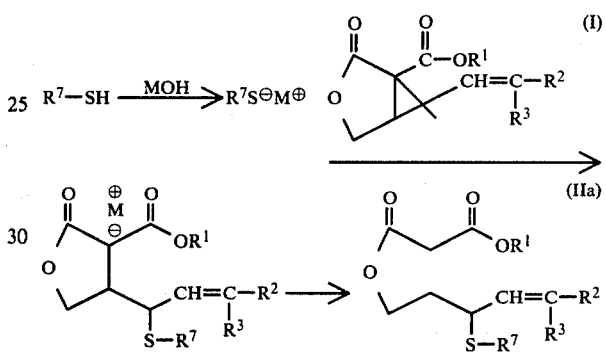

As is apparent to one skilled in the art, a mercaptide anion corresponding to the mercaptan compound of the formula (V) also have the same function as the mercaptan compound, and thus the present invention also includes the use of such mercaptide anions in the reaction with the compound of the formula (I).

In carrying out the reaction between the bicyclolactone compound of the formula (I) and the mercaptan compound of the formula (V), it is preferred to use a polar solvent which does not take part in the reaction and which is inert to the reactants used as well as to the desired product. Suitable examples of polar solvents are ethers such as diethyl ether, tetrahydrofuran and the like, alcohols such as methanol, ethanol, t-butanol and the like, dimethylformamide, acetonitrile, dimethyl sulfoxide and the like.

The γ-lactone sulfide compound of the formula (IIa) thus obtained has a characteristic feature in that it easily reacts with an alkylating agent due to the presence of an ester group at the 2-position and yet it has a reactivity with an alkylating agent selectively at the 2-position.

Representative compounds of the γ-lactone sulfide compounds of the formula (IIa) are:
3-methoxycarbonyl-4-(1-phenylthio-trans-2-octenyl)-oxolane-2-one,
3-ethoxycarbonyl-4-(3-methyl-1-tolylthio-2-octenyl)-oxolane-2-one,
3-methoxycarbonyl-4-(1-methylthio-trans-2-octenyl)-oxolane-2-one, and the like.

The compound of the formula (IIb) can then be prepared from the γ-lactone sulfide compound of the formula (IIa) obtained as above by reacting the γ-lactone sulfide compound with an alkylating agent represented by the formula (VIII)

$$Z-R^5 \tag{VIII}$$

wherein Z represents a halogen atom, a tosyloxy group or an acyloxy group, $R^5$ represents a substituted or unsubstituted alkyl or alkenyl group of the formula $-CH_2-Y-(CH_2)_n-COOR^6$ wherein $R^6$, Y and n are as defined above, in the presence of a base.

The reaction between the γ-lactone sulfide compound of the formula (IIa) and the alkylating agent of the formula (VIII) can be carried out at a temperature of from about 0° C. to about 150° C., preferably at room temperature, for about 1 to about 24 hours, using an approximately equimolar amount of the alkylating agent of the formula (VIII) relative to the compound of the formula (IIa).

Representative alkylating agents of the formula (VIII) are methyl 7-chloroheptanoate, methyl 7-bromoheptanoate, methyl 7-iodoheptanoate, ethyl 7-iodoheptanoate, methyl 7-iodo-5-heptenoate, 1-iodo-6-(tetrahydropyranyloxycarbonyl)-hexane, methyl-7-chloro-5-heptenoate, methyl 7-bromo-5-heptenoate, ethyl 7-chloro-5-heptenoate, ethyl 7-bromo-5-heptenoate and the like.

Suitable examples of base which can be used in the above alkylation reaction are alkali metal carbonates such as potassium carbonate, sodium carbonate and the like, alkali metal hydroxides such as potassium hydroxide, sodium hydroxide and the like, alkali metal hydrides such as sodium hydride, potassium hydride and the like, alkali metal alkoxides such as sodium methoxide, potassium methoxide, sodium ethoxide, potassium t-butoxide and the like, and organic amines such as triethylamine, tributylamine, pyridine and the like. These bases can be used in an amount of approximately equimolar amount to slightly molar excess amount relative to the compound of the formula (IIa).

The alkylation reaction described above is advantageously carried out in an inert organic solvent which does not take part in the reaction and which is inert to the reactants as well as the desired compound. Suitable examples of solvents are alcohols such as methanol, ethanol, t-butanol and the like, ethers such as diethyl ether, tetrahydrofuran and the like, benzene, toluene, xylene, dimethylformamide, acetonitrile, dimethyl sulfoxide and the like.

Representative compounds of the γ-lactone sulfide compounds of the formula (IIb) thus obtained are:

3-methoxycarbonyl-3-(6-methoxycarbonylhexyl)-4-(1-phenylthio-trans-2-octenyl)-oxolane-2-one, 3-(6-ethoxycarbonyl-2-hexenyl)-3-methoxycarbonyl-4-(1-phenylthio-trans-2-octenyl)-oxolane-2-one, 3-methoxycarbonyl-3-(6-methoxycarbonylhexyl)-4-(3-methyl-1-methylthio-2-octenyl)-oxolane-2-one, and the like.

The compounds of the formulae (IIc) and (IIe) can be prepared from the compounds of the formulae (IIb) and (IIa), respectively, by removal of alkoxycarbonyl group attached to the 2-position of the lactone ring.

The removal of the alkoxycarbonyl group can be achieved by one of alternative procedures, i.e., (1) heat-treatment of the compound of the formula (IIb) or (IIa) in the presence of an alkali metal salt or (2) acid or alkali hydrolysis followed by heat-treatment.

The heat-treatment as described in (1) above can be effected at a temperature of about 50° to about 200° C., preferably 100° to 150° C., for a period of from about 30 minutes to about 3 hours, preferably in the presence of an inert polar solvent which does not take part in the reaction, for example, alcohols such as methanol, ethanol, t-butanol and the like, ethers such as diethyl ether, tetrahydrofuran and the like, amines such as pyridine, piperidine, colidine and the like, dimethylformamide, acetonitrile, dimethyl sulfoxide and the like. The time required for completing the removal of the alkoxycarbonyl group varies widely depending upon the type of the compound of the formula (IIb) or (IIa) and the alkali metal salt used as well as the temperature employed in the heat-treatment.

Suitable examples of alkali metal salts which can be used in the above heat-treatment (1) are alkali metal iodides and hydrates thereof such as sodium iodide, potassium iodide, lithium iodide and hydrates thereof, and alkali metal cyanides such as sodium cyanide, potassium cyanide, lithium cyanide and the like. Particularly preferred alkali metal salts from the standpoint of high yield of the desired product are lithium iodide or the hydrate thereof and sodium cyanide. The alkali metal salt can be used in an approximately equimolar amount relative to the compound of the formula (IIb) or (IIa) with a satisfactory result, but a larger or smaller amount of the alkali metal salt may be used.

In an alternative procedure for the removal of the alkoxycarbonyl group by acid or alkali hydrolysis, various acids or bases can be used. Examples of acids which can be used in the acid hydrolysis are inorganic acids such as hydrochloric acid, sulfuric acid, phosphoric acid and the like, and organic acids such as p-toluenesulfonic acid, acetic acid and the like. Examples of the bases which can be used for the alkali hydrolysis are alkali metal hydroxides such as sodium hydroxide, potassium hydroxide and the like, alkali metal carbonates such as sodium carbonate, potassium carbonate and the like. The acid can be used in a so-called catalytic amount in the acid hydrolysis, but the base can be preferably used in an approximately equimolar amount relative to the compound of formula (IIb) or (IIa).

The acid and alkali hydrolysis can be effected at a temperature of about 0° C. to about 150° C., preferably 50° to 100° C. for about 2 to about 24 hours.

Under hydrolysis conditions using an acid, the hydrolysis of an ester group and the decarbonization can be achieved simultaneously by heating the reaction system at the temperature set forth above, whereas under hydrolysis conditions using a base, only the ester group is removed and the resulting hydrolysis reaction mixture should be rendered neutral or weakly acidic and then subjected to the heat-treatment for decarbonization. In either cases, the time required for heat-treatment varies depending upon the type of the compound to be treated and the temperature used, but, heating for about 30 minutes to about 3 hours is generally sufficient.

The removal of alkoxycarbonyl group by acid or alkali hydrolysis can be preferably effected in an aqueous medium such as water, or a hydrated solvent such as hydrated tetrahydrofuran, acetone, alcohols and the like.

Typical examples of the compounds of the formulae (IIc) and (IIe) thus obtained are:

3-(6-methoxycarbonylhexyl)-4-(1-phenylthio-trans-2-octenyl)-oxolane-2-one, 3-(6-ethoxycarbonyl-2-hexenyl)-3-(1-methylthio-trans-2-octenyl)-oxolane-2-one, 3-(6-methoxycarbonylhexyl)-4-(3-methyl-1-phenylthio-2-octenyl)-oxolane-2-one, and the like.

The compound of the formula (IId) can be prepared from the the corresponding lactone sulfide compound of the formula (IIc) by oxidation using an oxidizing agent in an inert solvent at a temperature of about −30° to about 50° C., preferably at room temperature for about 1 to 3 hours.

Suitable examples of oxidizing agents which can be used for the above oxidation are inorganic oxidizing agents such as sodium iodate, hydrogen peroxide, oxygen, ozone, manganese dioxide, selenium dioxide, chromic acid, nitric acid, dinitrogen tetraoxide and the like, the organic oxidizing agents such as peracetic acid, perbenzoic acid, m-chloroperbenzoic acid, iodosobenzene and the like. Preferred organic oxidizing agents are organic peroxides described above, more preferably, m-chloroperbenzoic acid, since these peroxides do not adversely affect reactive groups present in the lactone sulfide compounds of the formula (IId), such as a carbonyl group and an ester group. The oxidizing agent can be used in an approximately equimolar amount relative to the compound of the formula (IIc).

Suitable examples of the inert solvents are water, alcohols such as methanol, ethanol and the like, ethers such as diethyl ether, tetrahydrofuran, dimethoxyethane and the like, acetic acid, chloroform, methylene chloride, benzene and the like, but other inert solvents which do not take part in the oxidation can be used as well.

Representative examples of the compounds of the formula (IId) are 4-(1-benzenesulfinyl-trans-2-octenyl)-3-(6-methoxycarbonylhexyl)-oxolane-2-one, 3-(6-ethoxycarbonyl-2-hexenyl)-4-(1-toluenesulfinyl-trans-2-octenyl)-oxolane-2-one, 4-(1-methanesulfinyl-3-methyl-2-octenyl)-3-(6-methoxycarbonylhexyl)-oxolane-2-one and the like.

The compounds of the formula (IId) thus obtained can be converted into the corresponding oxaprostaglandin derivatives by treating the compound with a reagent having "thiophilicity", i.e., a reagent having a high affinity for a sulfur atom, for example, organic amines such as triethylamine, diethylamine, pyridine and the like, organophosphorus compounds such as trimethyl phosphite, triethyl phosphite, trisdimethylaminophosphine and the like, and mercaptans, in an amount of approximately equimolar amount relative to the compound of the formula (IId), at a temperature of from about −30° C. to room temperature for about 2 to 24 hours in an inert solvent such as alcohols such as methanol, ethanol, t-butanol and the like, ethers such as diethyl ether, tetrahydrofuran and the like, dimethyl sulfoxide, hexamethylphosphoric triamide and the like.

The present invention is further illustrated by the following Reference Examples and Examples, but these examples are given for illustrative purposes only and are not to be construed as limiting the scope of the invention. All parts, percents, ratios and the like are by weight unless otherwise indicated.

REFERENCE EXAMPLE 1

6.08 g (40 mmols) of trans, trans-2,4-decadienal was dissolved in 50 ml of methanol and 379 mg (10 mmols) of sodium borohydride was added slowly to the solution while stirring and cooling at a temperature of 0° C. After disappearance of the starting material had been confirmed, the mixture was concentrated under reduced pressure. An aqueous solution of ammonium chloride was added to the mixture to decompose the complex compound formed, and the mixture was extracted with diethyl ether. The ethereal layer was washed with a saturated aqueous solution of sodium chloride and dried over anhydrous magnesium sulfate. The extract was then filtered and the filtrate was concentrated under reduced pressure. The residue thus obtained was distilled under reduced pressure to obtain 5.08 g (83% yield) of trans, trans-2,4-decadienol as an oily substance having a boiling point of 75°-87° C./0.3 mmHg.

Infrared Absorption Spectrum (cm$^{-1}$): 3300, 1655, 1465, 1375, 1085, 985.

NMR Absorption Spectrum (CDCl$_3$)δ: 0.88 (t, J=6 Hz, 3H), 1.07-1.56 (m, 6H), 1.82 (broad s, 1H), 2.00 (t, J=6 Hz, 2H), 4.08 (broad d, J=6 Hz, 2H), 5.24-6.38 (m, 4H).

REFERENCE EXAMPLE 2

4.72 g (39 mmols) of dimethylaniline was added to a solution of 4.26 g (30 mmols) of trans, trans-2,4-decadienol dissolved in 35 ml of anhydrous diethyl ether followed by stirring. Then, a solution of 4.15 g (39 mmols) of malonic acid methyl ester chloride dissolved in 35 ml of anhydrous diethyl ether was added dropwise to the above-prepared solution while cooing with ice. The mixture was heated while refluxing for 3 hours and, thereafter, cooled to room temperature. Diethyl ether and water were added to the reaction mixture and the resulting mixture was extracted with ethyl acetate. The extract was washed successively with a 10% aqueous sulfuric acid solution and a saturated aqueous solution of sodium bicarbonate, and dried over anhydrous magnesium sulfate. The resulting extract was filtered and the filtrate was concentrated. The residue was purified by silica gel column chromatography using a mixture of ethyl acetate and n-hexane (1:9 by volume) as an eluent to obtain 6.78 g (89% yield) of methyl, trans, trans-2,4-decadienyl malonate.

Infrared Absorption Spectrum (cm$^{-1}$): 1760, 1738, 1659, 1273, 1048, 1020, 990.

NMR Absorption Spectrum (CCl$_4$)δ: 0.88 (t, J=5 Hz, 3H), 1.15-1.80 (m, 6H), 1.82-2.50 (m, 2H), 3.17 (s, 2H), 3.70 (s, 3H), 4.57 (d, J=3 H, 2H), 5.22-6.60 (m, 4H).

Mass Spectrum m/e (%): 254 (2), 101 (100), 80 (52), 79 (77), 67 (60), 59 (54).

REFERENCE EXAMPLE 3

1.30 g (5 mmols) of methyl malonate trans, trans-2,4-decadienyl prepared as described in Reference Example 2 above and 0.99 g (5 mmols) of p-toluenesulfonyl azide were dissolved in 5 ml of acetonitrile and 0.51 g (5 mmols) of triethylamine dissolved in 3 ml of acetonitrile were added while cooling with ice. The mixture was allowed to warm to room temperature and stirred for 19 hours. After completion of the reaction, a 1/3 volume of the acetonitrile used was removed under reduced pressure, and the reaction mixture was washed 3 times with a 5% aqueous solution of potassium hydroxide. The reaction mixture was further washed with a saturated aqueous sodium chloride solution and then dried over anhydrous magnesium sulfate. The solvent was removed under reduced pressure to obtain 1.38 g of methyl, trans, trans-2,4-decadienyl diazomalonate as an oily substance. The resulting crude product was found to be substantially pure, but for analysis a sample of the product obtained was purified by silica gel column chromatography using a mixture of ethyl acetate and n-hexane (1:9 by volume) as an eluent.

Infrared Absorption Spectrum (cm$^{-1}$): 2125, 1765, 1740, 1075, 990, 760

NMR Absorption Spectrum (CCl$_4$)δ: 0.89 (t, J=6 Hz, 3H), 1.10-1.65 (m, 6H), 1.84-2.27 (m, 2H), 3.77 (s, 3H), 4.65 (d, J=3 Hz, 2H), 5.40-6.44 (m, 4H).

REFERENCE EXAMPLE 4

1.80 g (4.03 mmols) of 3-(6-methoxycarbonylhexyl)-4-(1-phenylthio-trans-2-octenyl)-oxolane-2-one was dissolved in 20 ml of absolute methanol. A solution of 818 mg (4.03 mmols) of m-chloroperbenzoic acid (85% purity) dissolved in 6 ml of methanol was added dropwise to the solution in an argon atmosphere while stirring and cooling at a temperature of −10° to −20° C. After stirring for 30 minutes, a solution of 2.50 g (20.15 mmols) of trimethyl phosphite in 6 ml of methanol was added dropwise to the reaction mixture which was then stored overnight in a refregerator. Most of the methanol was removed from the reaction mixture under waterstream reduced pressure, and 50 ml of ethyl acetate was added to the mixture. The resulting mixture was washed with an aqueous solution of sodium chloride and dried over anhydrous magnesium sulfate. The resulting residue was purified by silica gel column chromatography using a mixture of ethyl acetate and n-hexane (3:7 by volume) as an eluent to obtain 104 mg of an oily substance as a first fraction having a relatively low polarity and 958 mg of an oily substance as a second fraction having a relatively high polarity [15(S)-hydroxy-9-oxo-13,14-didehydro-(trans)-10-oxa-prostanoic acid methyl ester]. The total yield of the product was 67%. The first and the second fractions were found to have almost the same spectra described hereinbelow. Infrared Absorption Spectrum (cm$^{-1}$): 1775, 1735, 1160, 1018, 970.

NMR Absorption Spectrum (CCl$_4$)δ: 0.87 (t, J=6 Hz, 3H), 1.00-2.40 (m, 21H), 2.56-2.94 (m, 1H), 2.69 (broad s, 1H), 3.55 (s, 3H), 3.85-4.02 (m, 1H), 3.74 (t, J=8 Hz, 1H), 4.09 (t, J=8 Hz, 1H), 5.30-5.70 (m, 2H).

Mass Spectrum m/e (%): 289 (19), 251 (100), 223 (46), 218 (53), 109 (96).

The second fraction having a higher polarity obtained as described above was hydrolyzed in accordance with a known method as described in Japanese Patent Application Laid Open to Public No. 8773/1973 to obtain 15(S')-hydroxy-9-oxo-13,14-didehydro-(trans)-10-oxa-prostanoic acid having a melting point of 59° C. The infrared and NMR absorption spectra of the resulting compound were found to be quite consistent with those described in the literature.

EXAMPLE 1

6.52 g (23 mmols) of methyl, trans, trans-2,4-decadienyl malonate as prepared in Reference Example 3 above was dissolved in 200 ml of toluene and the solution was heated while refluxing and stirring for 24 hours in the presence of 5.0 g of copper powder. The reaction mixture was cooled to room temperature and filtered to remove copper powder. The solvent was removed from the filtrate under reduced pressure and the resulting residue was purified by silica gel column chromatography using a mixture of ethyl acetate and n-hexane (1:9 by volume) as an eluent to obtain 3.75 g (64% yield) of methyl exo-6-(trans-1-heptenyl)-3-oxa-2-oxo-bicyclo[3.1.0]hexane-1-carboxylate as an oily substance.

Infrared Absorption Spectrum (cm$^{-1}$): 1780, 1725, 1240, 1050, 960.

NMR Absorption Spectrum (CCl$_4$)δ: 0.87 (t, J=6 Hz, 3H), 1.10-1.60 (m, 6H), 1.84-2.14 (m, 2H), 2.18 (dd, J=5, 8 Hz, 1H), 2.63 (t, J=5 Hz, 1H), 3.69 (s, 3H), 4.09 (d, J=9 Hz, 1H), 4.26 (dd, J=5, 9 Hz, 1H), 5.22 (dd, J=8, 15 Hz, 1H), 5.73 (dt, J=7, 15 Hz, 1H).

Mass Spectrum m/e (%): 252 (3), 150 (51), 105 (52), 91 (71), 79 (79), 77 (54), 67 (51), 59 (64), 55 (50), 41 (100).

EXAMPLE 2

280 mg (1 mmol) of methyl, trans, trans-2,4-decadienyl diazomalonate was dissolved in 10 ml of benzene, and 200 mg of cuprous cyanide was added to the solution. The mixture was then heated while refluxing for 5 hours with vigorous stirring. The resulting reacting mixture was then worked up in the same manner as described in Example 1 to obtain 182 mg (72% yield) of methyl exo-6-(trans-2-heptenyl)-3-oxa-2-oxo-bicyclo[3.1.0]hexane-1-carboxylate.

EXAMPLE 3

448 mg (4 mmols) of potassium t-butoxide was added to 25 ml of t-butanol in an argon atmosphere followed by stirring. Then, a solution of 440 mg (4 mmols) of thiophenol dissolved in 5 ml of t-butanol was added to the solution followed by stirring for 10 minutes. Thereafter, 1.0 g (4 mmols) of methyl exo-6-(trans-1-heptenyl)-3-oxa-2-oxo-bicyclo[3.1.0]hexane-1-carboxylate dissolved in 5 ml of t-butanol was added to the mixture followed by stirring for 3 hours at room temperature. The resulting mixture was treated with an aqueous solution of ammonium chloride and extracted with ethyl acetate. The extract was washed with a saturated aqueous solution of sodium chloride and dried over anhydrous magnesium sulfate. The mixture was filtered and the filtrate was concentrated. The resulting residue was purified by silica gel column chromatography using a mixture of ethyl acetate and n-hexane (1:9 by volume) as an eluent to obtain 870 mg (60% yield) of 3-methoxycarbonyl-4-(1-phenylthio-trans-2-octenyl)-oxoran-2-one as an oily substance.

Infrared Absorption Spectrum (cm$^{-1}$): 1788, 1743, 1256, 1147, 1016, 970.

NMR Absorption Spectrum (CCl$_4$)δ: 0.86 (t, J=6 Hz, 3H), 1.00-1.45 (m, 6H), 1.62-2.20 (m, 2H), 2.94-3.58 (m, 3H), 3.71 (s, 3H), 4.09 (dd, J=7.9 Hz, 1H), 4.50 (dd, J=7,9 Hz, 1H), 5.02-5.46 (m, 2H), 7.00-7.58 (m, 5H).

Mass Spectrum m/e (%): 362 (13), 209 (100), 135 (65), 110 (85), 109 (73).

EXAMPLE 4

2.88 g (7.94 mmols) of 3-methoxycarbonyl-4-(1-phenylthiotrans-2-octenyl)-oxolane-2-one and 0.98 g (8.73 mmols) of potassium t-butoxide were dissolved in 47 ml of dimethyl sulfoxide in an argon atmosphere and the mixture was stirred for 10 minutes at room temperature. A solution of 2.36 g (8.73 mmols) of methyl 7-iodoheptanoate in 3 ml of dimethyl sulfoxide was added to the above reaction mixture followed by stirring for 19 hours at room temperature. The reaction mixture was then rendered neutral with diluted hydrochloric acid while cooling with ice-water and extracted with ethyl acetate. The extract was washed with a saturated aqueous solution of sodium chloride and dried over anhydrous magnesium sulfate. The extract was filtered and the solvent was removed from the filtrate under reduced pressure. The residue thus obtained was purified by silica gel column chromatography using a mixture of ethyl acetate and n-hexane as an eluent to obtain 3.93 g (98% yield) of 3-methoxycarbonyl-3-(6-methoxycarbonylhexyl)-4-(1-phenylthio-trans-2-octenyl)-oxolane-2-one as an oily substance.

Infrared Absorption Spectrum (cm$^{-1}$): 1780, 1741, 1725, 1215, 1075, 1020, 970.

NMR Absorption Spectrum (CCl$_4$)δ: 0.84 (t, J=6 Hz, 1H), 0.96-2.35 (m, 20H), 2.48-2.96 (m, 1H), 3.30-3.51 (m, 1H), 3.55 (s, 3H), 3.64 (s, 3H), 4.04-4.61 (m, 2H), 4.80-5.36 (m, 2H), 7.00-7.60 (m, 5H).

Mass Spectrum m/e (%): 504 (trace), 363 (61), 135 (100).

EXAMPLE 5

1.00 g (1.98 mmol) of 3-methoxycarbonyl-3-(6-methoxycarbonylhexyl)-4-(1-phenylthio-trans-2-octenyl)-oxolane-2-one was dissolved in 23 ml of hexamethylphosphoric triamide followed by stirring. 194 mg (3.96 mmols) of sodium cyanide was then added to the solution and the mixture was heated at 75° to 80° C. for 15 hours while heating. The mixture was allowed to cool to room temperature and rendered neutral with diluted hydrochloric acid. The mixture was extracted with ethyl acetate and the extract was washed three times with water and dried over anhydrous magnesium sulfate. The solvent was then removed by distillation and the resulting residue was purified by silica gel column chromatography using ethyl acetate and n-hexane (1:9 by volume) as an eluent to obtain 730 mg (83% yield) of 3-(6-methoxycarbonylhexyl)-4-(1-phenylthio-trans-2-octenyl)-oxolane-2-one an an oily substance.

Infrared Absorption Spectrum (cm$^{-1}$): 1780, 1740, 1178, 1025, 970.

NMR Absorption Spectrum (CCl$_4$)δ: 0.84 (t, J=6 Hz, 3H), 0.96-2.65 (m, 22H), 3.38-3.53 (m, 1H), 3.58 (s, 3H), 4.08 (dd, J-8, 10 Hz, 1H), 4.32 (dd, J=9, 10 Hz, 1H), 5.04-5.40 (m, 2H), 7.00-7.51 (m, 5H).

Mass Spectrum m/e (%): 447 (3), 446 (8), 305 (100).

EXAMPLE 6

60 mg (0.17 mmol) of 3-methoxycarbonyl-4-(1-phenylthio-trans-2-octenyl)-oxolane-2-one was dissolved in 2 ml of hexamethyl phosphoric triamide in an argon atmosphere, and 36 mg (0.85 mmol) of lithium chloride was added to the solution followed by heating at a temperature of 100° C. for 5 hours with stirring. The reaction mixture was then allowed to cool to room temperature and decomposed with dilute hydrochloric acid. The mixture was extracted with ethyl acetate, and the extract was washed with a saturated aqueous solution of sodium chloride and dried over anhydrous magnesium sulfate. The mixture was filtered and the filtrated was concentrated under reduced pressure. The resulting residue was then purified by silica gel column chromatography to obtain 4-(1-phenylthio-trans-2-octenyl)-oxolane-2-one.

Infrared Absorption Spectrum (cm$^{-1}$): 1780, 1298, 1168, 983, 748, 690.

EXAMPLE 7

166 mg (0.33 mmol) of 3-methoxycarbonyl-3-(6-methoxycarbonylhexyl)-4-(1-phenylthio-trans-2-octenyl)-oxolane-2-one was dissolved in 4 ml of hexamethylphosphoric triamide in an argon atmosphere followed by stirring. 70 mg (1.65 mmols) of lithium chloride was then added to the solution and the mixture was stirred at a temperature of 100° C. for 5 hours. The resulting mixture was then worked up in the same manner as described in Example 5 to obtain 61 mg (41% yield) of 3-(6-methoxycarbonylhexyl)-4-(1-phenylthio-trans-2-octenyl)oxolane-2-one.

EXAMPLE 8

447 mg (1 mmol) of 3-(6-methoxycarbonylhexyl)-4-(1-phenylthio-trans-2-octenyl)-oxolane-2-one was dissolved in 5 ml of absolute methanol, and a solution of 204 mg (1 mmol) of m-chloro benzoic acid (85% purity) dissolved in 3 ml of methanol was added to the solution in an argon atmosphere while cooling at a temperature of −20° C. and stirring. After allowing the mixture to stand for one hour, ammonia gas was bubbled into the reaction mixture to convert m-chlorobenzoic acid formed as a by-product into an ammonium salt thereof, and most of the solvent was removed by distillation. The resulting residue was then extracted with ethyl acetate, and the extract was washed with water and dried over anhydrous magnesium sulfate. The extract was filtered and the filtrate was concentrated under reduced pressure. The residue thus obtained was purified by silica gel column chromatography to obtain 384 mg of 3-(6-methoxycarbonylhexyl)-4-(1-benzenesulfinyl-trans-2-octenyl)-oxolane-2-one.

Infrared Absorption Spectrum (cm$^{-1}$): 1780, 1740, 1040, 970.

While the invention has been described in detail and with reference to specific embodiments thereof, it will be apparent to one skilled in the art that various changes and modifications can be made therein without departing from the spirit and the scope thereof.

What is claimed is:

1. A process for preparing a compound of the formula (IId)

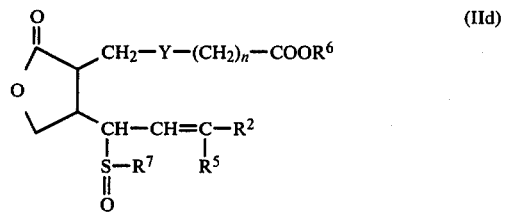

wherein R$^2$ represents a straight or branched chain substituted or unsubstituted alkyl group having 1 to 8 carbon atoms wherein the substituent is an —O-alkyl group or a —S-alkyl group wherein the alkyl moiety can be a straight or branched chain having 1 to 4 carbon atoms, or is a phenoxy group which may be substituted with a halogen atom or an alkyl group having 1 to 4 carbon atoms, R$^3$ represents a hydrogen atom or an alkyl group having 1 to 4 carbon atoms, R$^6$ represents a hydrogen atom or an alkyl group having 1 to 4 carbon atoms, R$^7$ represents an alkyl group having 1 to 4 carbon atoms or an unsubstituted or substituted phenyl group wherein the substituent is a halogen atom, or an alkyl or alkoxy group having 1 to 4 carbon atoms, Y represents a —CH$_2$CH$_2$— group or a —CH=CH— group, and n is an integer of 0 to 6, which comprises subjecting a diazomalonic acid ester represented by the formula (VI)

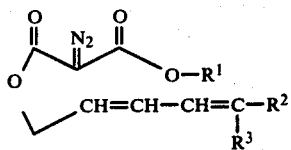

(VI)

wherein $R^2$ and $R^3$ are as defined above and $R^1$ represents an alkyl group having 1 to 4 carbon atoms, to a carbene or carbenoid formation either by a catalytic reaction or a photo-decomposition to produce a bicyclolactone compound of the formula (I)

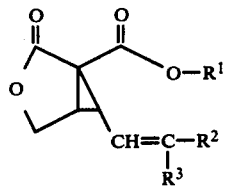

(I)

wherein $R^1$, $R^2$ and $R^3$ are as defined above, reacting the thus obtained bicyclolactone compound with a mercaptan compound of the formula (VII)

$R^7$-SH  (VII)

wherein $R^7$ is as defined above, in the presence of a base to produce a γ-lactone sulfide compound of the formula (IIa)

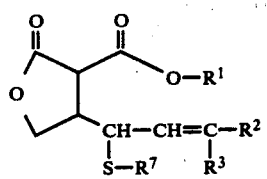

(IIa)

wherein $R^1$, $R^2$, $R^3$ and $R^7$ are as defined above, reacting the thus obtained γ-lactone sulfide compound with an alkylating agent of the formula (VIII)

$Z-CH_2Y-(CH_2)_n-COOR^6$  (VIII)

wherein $R^6$, Y and n are as defined above, and Z represents a halogen atom, a tosyloxy group or an acyloxy group, in the presence of a base to produce a compound of the formula (IIb)

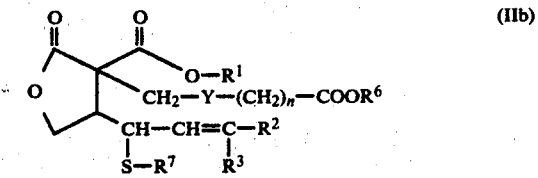

(IIb)

wherein $R^1$, $R^2$, $R^3$, $R^6$, $R^7$, Y and n are as defined above, subjecting the thus obtained compound of the formula (IIb) to either (1) heat-treatment at a temperature of about 50° to about 200° C. in the presence of an alkali metal compound and inert polar solvent, or (2) an acid or alkali hydrolysis at a temperature of about 0° C. to about 150° C. followed by heat treatment at a temperature of about 50° C. to about 200° C. to produce a compound of the formula (IIc)

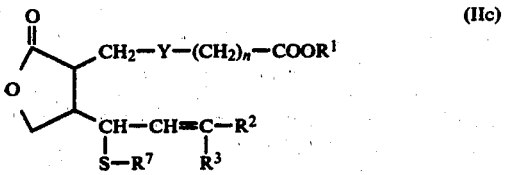

(IIc)

wherein $R^2$, $R^3$, $R^6$, $R^7$, Y and n are as defined above, and oxidizing the thus obtained compound of the formula (IIc) with an oxidizing agent in an inert solvent.

* * * * *